United States Patent [19]

Dardik et al.

[11] 4,250,887

[45] Feb. 17, 1981

[54] REMOTE MANUAL INJECTING APPARATUS

[75] Inventors: Herbert Dardik; Michael Smith; Ibrahim M. Ibrahim; Irving I. Dardik, all of Tenafly, N.J.

[73] Assignee: Dardik Surgical Associates, P.A., Fort Lee, N.J.

[21] Appl. No.: 31,173

[22] Filed: Apr. 18, 1979

[51] Int. Cl.³ .............................................. A61B 5/02
[52] U.S. Cl. ................................ 128/655; 128/218 A
[58] Field of Search ............... 128/218 A, 218 R, 655, 128/215, 216, 224

[56] References Cited

U.S. PATENT DOCUMENTS

| | | | |
|---|---|---|---|
| 3,491,749 | 1/1970 | Gidlund | 128/655 |
| 3,523,523 | 8/1970 | Reich et al. | 128/655 |
| 3,880,138 | 4/1975 | Wootten et al. | 128/655 |

*Primary Examiner*—John D. Yasko
*Attorney, Agent, or Firm*—J. David Dainow

[57] ABSTRACT

An apparatus for injecting a radiopaque dye into an artery of a patient during intraoperative arteriography, where the plunger of a syringe containing the injectate is driven by a separate but connected hydraulic sub-system operated by a surgeon who is at a location that is remote and safe from the radiation, and where the hydraulic sub-system provides for the surgeon, the feel and control of a conventional syringe operated manually in the immediate vicinity of the patient.

7 Claims, 3 Drawing Figures

U.S. Patent  Feb. 17, 1981  4,250,887
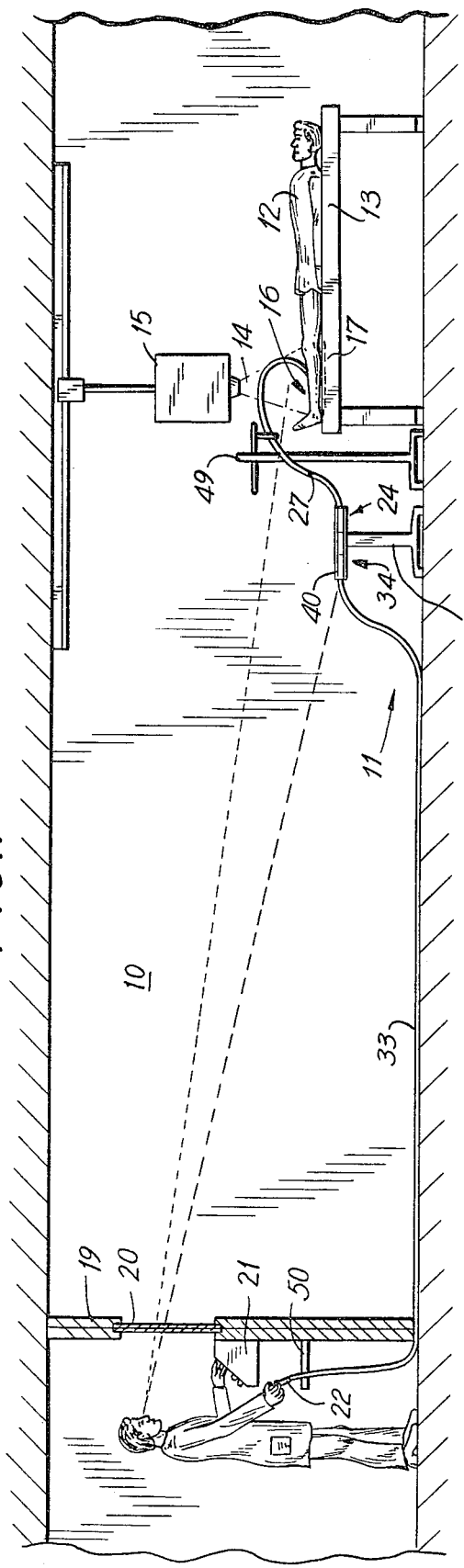
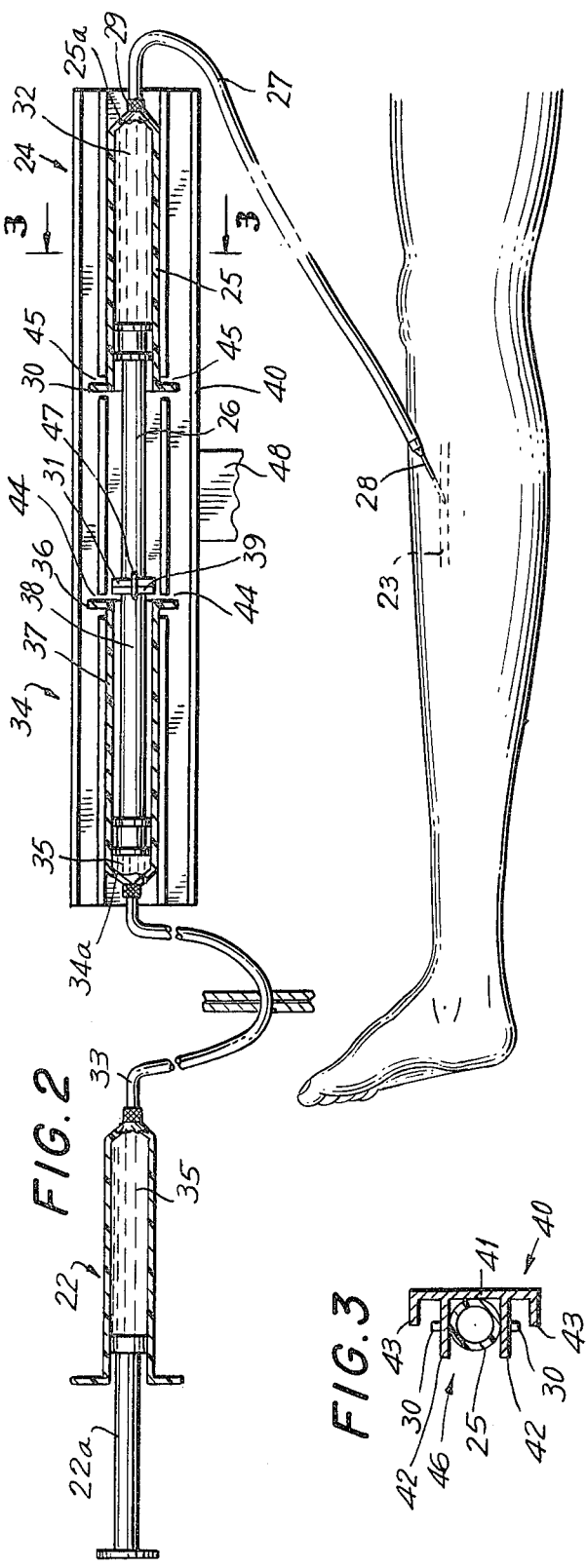

REMOTE MANUAL INJECTING APPARATUS

BACKGROUND OF THE INVENTION

This invention concerns intraoperative angiography for vascular reconstructive surgery, and more particularly, apparatus for injecting radiopaque dye into a new artery during arteriography.

Vascular reconstructive surgery has progressed significantly in recent years with the development of new surgical techniques producing obvious benefits to the patients involved. A detailed description of this surgery will not be attempted here, because this patent application concerns apparatus used in conjunction with such surgery and presumes a reasonable familiarity with the basic surgical procedures.

While pre-operative arteriograms are normally obtained and utilized in connection with vascular reconstruction, intra-operative arteriography (also abbreviated "IOA") has not become routinely practiced for various reasons, including the belief by some surgeons that intraoperative arteriography is not necessary, and the concern by surgeons for the damage to their personal health due to the cumulative effects of repeated radiation exposure they experience, should they conduct IOA with every arterial reconstructive procedure. The more recent experience with IOA indicates strongly that this procedure is more than merely useful, and in many cases will provide critical information that will call for immediate corrective surgery. More particularly, IOA can provide immediate identification of technical errors at the suture line, platelet thrombi, atherosclerotic debris, previously unrecognized or unappreciated stenosing lesions just beyond the distal anastomosis, or rotation or kinking of the graft, thereby enabling the immediate corrective surgery. Subsequent or unrecognized graft failure is thus obviated; unrecognized bleeding can also be found if extravascular pooling of the contrast medium occurs, particularly at sites remote from insertion of the needle used for the angiogram. The value of IOA in cases of vascular trauma is also evident, particularly to avoid constricting anastomosis in medium-sized or small arteries and to delineate unrecognized areas of injury. Further description of these known medical procedures is found in the article, "Routine Intraoperative Angiography" in Archives of Surgery, Volume 110, February, 1975, by Irving I. Dardik, M.D., et al.

The basic problem considered herein is the radiation exposure experienced by the surgeon during intraoperative arteriography because he is very close to the patient while he manually injects the radiopaque dye into the patient's artery, as x-ray radiation is directed to the area of vascular reconstruction. Even though the x-ray beam is collimated and the surgeon wears a lead vest or apron, there remains some radiation danger due to imperfect collimation and/or scatter, which on a cummulative basis can be detrimental.

The reason for the surgeon's close proximity to the radiation is the requirement for his personal and continuous control of the injection which he can maintain by virtue of his direct observation and his "feel" of the injectate flow and/or resistance to flow while the syringe plunger is operated by his thumb and fingers. With regard to this radiation danger, obviously the surgeon and his operating team feel more confident and clearly are more safe when they retreat behind a lead-lined wall or leaded glass window while the x-ray radiation occurs. Unfortunately the surgeon cannot carry out personal, manual injection while he is at a remote location.

One might consider a remote, electronically controlled injecting device which is invulnerable to x-ray radiation and which is operated by switches and levers in the radiation-safe location. While attractive in theory, such is not really feasible for the following reasons. A patient who receives the radiopaque dye during IOA is in the midst of surgery with new untested arterial grafts or other vascular reconstruction. An existing injecting machine such as the "Angiomat 3000" is designed for pre-operative angiography, where the injection rate is pre-set to be automatic and thus does not have features to sense and react properly to the many possible problems that could have developed or been discovered during surgery. Such a machine not only lacks the surgeon's versatility, it was not designed to deal with the intraoperative conditions. In fact, no machine is known that is able to register and simulate the surgeon's experienced "feel", judgment and reactions. Cost of equipment in medical care is another factor that must not be dismissed; highly expensive apparatus is avoided when not proven to be essential, and the problem or danger remains until a less expensive solution is found.

One might also consier providing a hose of about a 30-foot length filled with radiopaque injectate, with a needle on the remote end for insertion in the artery and a syringe on the near end behind the lead wall. This is highly impractical as it would require a fluid system starting in the non-sterile hallway with its destination in the patient's artery, via a hose lying on the floor or draped from one IV pole to another; also this would consume an excessive quantity of radiopaque dye to fill the entire length of hose, while only a small portion of the fluid would actually be injected.

For the reasons discussed above, intraoperative arteriography has not become a routine procedure; however the available evidence indicates IOA should become the rule rather than the exception. The present invention as described in subsequent sections, is an apparatus that permits the surgeon to have the benefits of conventional, manual injection in the immediate proximity of the patient during IOA, while he is actually at a remote location and behind lead-lined walls and safe from radiation. The invention is summarized below, followed by a detailed description of a preferred embodiment.

SUMMARY OF THE INVENTION

The present invention provides a system whereby a surgeon can manually, with conventional force and feel, cause injection of a radiopaque dye during angiography while remaining in a radiation-safe area remote from the patient and without actually touching the injectate syringe. The new apparatus, in combination with visual observation from the remote location, allows the surgeon to conduct intraoperative arteriography efficiently, precisely, and safely.

As illustrated herein a preferred embodiment combines with an injectate syringe, a hydraulic conduit, preferably flexible hose containing a fluid such as water or oil, which might have a density and viscosity generally similar to that of the radiopaque injectate. The conduit has a first end in the radiation-safe area with a conventional-type syringe for driving the hydraulic fluid in the conduit in the direction of the remote end which is situated very near the syringe containing injectate; a second, driven syringe is connected to the remote end, but oriented opposite the drive syringe, whereby the driven syringe's plunger is driven outward of the barrel when the drive syringe is operated to force fluid toward the remote end.

The invention further includes a fixture for holding the driven syringe barrel and injectate syringe barrel in an axial and fixed relationship, and a coupling for engaging the driven syringe plunger with the injectate syringe plunger. When so coupled the driven plunger, when moved axially, will drive the injectate plunger essentially the same distance and at the same rate in an ideal hydraulic system; normally, this coupling also permits reverse movement of the component.

With an apparatus as described above, the drive syringe and plunger are not only visually familiar to the surgeon, but they are and feel identical to the conventional injectate syringe. Modifications may be made if necessary in the dimensions of the drive and driven syringes and intermediate hose filled with fluid, to be sure they simulate closely the feel of direct manual injection of radiopaque dye, in regard to the mass and viscosity of the dye and the force to discharge same.

Not only does this new invention provide an apparatus that allows "manual" injection from a remote and radiation-safe location, it is extremely simple to use and inexpensive to manufacture; even standard syringes and tubing can be used until such time that commercial versions are available which have integrated the necessary components into complete, ready-to-use systems. The existence of these various advantages has led to rapid and enthusiastic acceptance of this invention by the surgical team using early versions thereof; without this invention intraoperative angiography had not become and was not becoming a routine procedure, despite the significant and important benefits that were clearly available.

A preferred embodiment of the invention is described below with reference to the appended drawing, however other versions are of course possible within the concept and spirit of the invention.

DESCRIPTION OF THE FIGURES AND THE PREFERRED EMBODIMENT

FIG. 1 is a fragmentary front elevation view showing the new remote manual injecting apparatus in use with a patient in an operating room;

FIG. 2 is an enlarged front elevation view partly in section of the apparatus of FIG. 1;

FIG. 3 is a sectional view taken along line 3—3 in FIG. 2;

FIG. 1 shows a portion of an operating room 10 with the new remote manual injecting apparatus 11 in use on a patient 12 on the operating table 13. Intraoperative arteriography is in process with the x-ray beam 14 directed downward from the radiation source 15 to the area 16 of vascular reconstruction, with x-ray film 17 in a cassette beneath the table surface or on the table but beneath the leg. The surgeon 18 is standing safely behind a lead-lined wall 19 and observing through a leaded window 20. By control panel 21 the surgeon can operate the x-ray source 15, and by syringe 22 he can manually cause injection of radiopaque dye into the reconstructed artery 23 (see FIG. 2) as will be described in detail in subsequent paragraphs.

The new apparatus includes a first or injectate syringe 24 of a conventional type comprising a barrel 25, a plunger 26, a flexible tube 27, needle 28, and an adapter 29 which could receive needle 28 directly in place of tube 27. The barrel 25 has wings 30, and the plunger 26 has a flanged end part 31. Within the barrel is radiopaque fluid 32 for injection into the artery 23. Further components of this invention include the hose 33 shown full length in FIG. 1, and shortened for convenience in FIG. 2, a second or drive syringe 22, a third or driven syringe 34, and a quantity of hydraulic fluid 35 filling hose 33 and partially filling the syringes 22 and 34 as indicated in FIG. 2. For convenience all three syringes 22, 34 and 24 may be standard, disposable medical syringes, each having a 50 cc capacity and the same basic components. Accordingly syringe 34 has wings 36 extending from its barrel 37, and plunger 38 with its flanged end part 39.

A fixture 40 provides support for driven syringe 34 and the injectate syringe 24, but also maintains these syringes in the necessary spaced relationship relative to each other, so that essentially identical movement by one can be transferred to the other. While fixture 40 may take any of a great many forms, the component illustrated in FIGS. 2 and 3 is an aluminum extrusion having bottom wall 41, side walls 42 approximately 1¼ inches wide and 20 inches long defining a U-shaped groove or trough 46, and outer flanges 43. The syringes 34 and 24 are placed in the groove 46, such that they are axially aligned but their discharge ends 34a and 25a respectively are directed oppositely, and their plungers 38 and 26 respectively are adjacent, with their flanged end parts 39 and 31 touching and secured together by coupling means 47. The wings 36 and 30 of the two syringe barrels fit into slots 44 and 45 respectively which fix the axial relationship of the two syringe barrels; with the plungers 38 and 26 also locked together, any axial movement of one plunger will force identical axial movement of the other.

In order for this apparatus to be conveniently used in different locations with different patients, the syringes are readily removable from groove 46, but when inserted in the groove are secure either by friction or additional holding means. Also coupling means 47 is firm and reliable, but is readily releasable for assembly, disassembly or adjustment of the components. The fixture 40 may be supported on its own stand 48 or on a standard IV pole as shown in FIG. 2; an additional IV pole 49 may be used to support the median portion of tube 27 leading to the patient's artery. The hydraulic fluid in the syringes 22 and 34 and the intermediate hose 33 is an inexpensive liquid such as distilled water or light oil which is purged of air; the radiopaque dye in syringe 24 is a standard fluid for this procedure, such as 50% diatrizoate sodium.

In the operation of this apparatus the plunger 22a of the drive syringe 22 is placed in the withdrawn position, the plunger 38 of the driven syringe 34 in the fully depressed position, the intermediate hose 33 filled with hydraulic fluid, and the fluid ducts purged of air or other gas. Syringe 24 is appropriately filled with radiopaque dye and is secured in groove 46 with its plunger 26 in the extended position and securely coupled to plunger 38 of the driven syringe 34. After verifying proper operation of the entire system and absence of any gas in any liquid space, the needle 28 is inserted in the artery above the site of reconstruction. With these preparations completed, the surgeon and operating team may take new positions behind wall 19 as shown in FIG. 1, and operate the x-ray machine by control panel 21 and proceed with dye injection by depressing the plunger of the drive syringe 22 supported by fixture 50. From this position the surgeon can observe both the area of vascular reconstruction and the coupled syringes; at the same time he has the personal control by virtue of the familiar, manual "feel" of the syringe and plunger, of the fluid flow and/or resistance to the flow.

It should be apparent that the drive and driven syringes and intermediate hose could be replaced with any fluid conduit having a drive piston at the near end and a driven piston at the remote end. The needle used in the above-described preferred embodiment is a 19 guage scalp vein needle and the hose is ⅜ inch in diamete TYGON tubing approximately 25 feet long, with which the overall apparatus functioned well. In an idealized hydraulic system the fluid conduit would be nonstretchable in both the axial and circumferential directions, in order for the input force and motion to be transmitted without distortion or reduction to the output end. The plastic tubing used in the above-described example is flexible and slightly elastic, and, accordingly, one would not expect such to be particularly suitable for the present device. It was discovered, however, that the objective of controlled remote injection could be achieved even with an imperfect hydraulic system. With this discovery it was possible to use very inexpensive and readily available tubing to construct efficient and satisfactory prototype versions of the new invention. One could obviously reduce or eliminate distortion of the conduit by using rigid pipe or the less extreme alternative of nylon-reinforced polyvinylchloride tubing, all still within the broader scope of this invention.

As indicated earlier, the fixture 40 of this hydraulic system also could take other forms, so long as the housing of the driven piston or plunger is fixed relative to the injectate barrel or housing, and the driven piston is fixedly or releasably secured or otherwise coupled to the injectate piston. The above-described apparatus is only one embodiment of many possibilities for manual injection by a person remote from the patient, within the scope and spirit of the claims following.

What is claimed is:

1. Apparatus for injecting radiopaque dye into a patient's artery during arteriography comprising a first syringe including a barrel for containing a quantity of said radiopaque dye, a first plunger for driving said dye out of said barrel, and a needle for introducing said dye from said barrel into the patient's artery, a conduit having opposite ends, second and third syringes having second and third barrels respectively, each with a discharge opening connected to one end of said conduit, a drive plunger in said second barrel and a driven plunger in said third barrel, said second and third syrings and intermediate conduit adapted to be filled with a generally imcompressible hydraulic fluid, whereby axial movement of the drive plunger will cause similar movement of the driven plunger, and coupling means for holding said first barrel and connecting said driven and first plungers, whereby axial movement of said driven plunger will drive said first plunger axially relative to said first barrel and discharge said dye out of said needle.

2. Apparatus according to claim 1 wherein said first barrel has a discharge opening, and said first syringe further comprises a flexible tube situated between said first barrel and said needle, said tube having a first end communicating with said discharge opening and an opposite end communicating with said needle.

3. Apparatus according to claim 1 wherein said coupling means comprises a fixture for holding said first and third barrels oriented in general alignment with their respective discharge openings facing in opposite directions and their respective plungers having external ends adjacent to each other, and connection means for securing these external ends together such that axial movement of one plunger causes the same axial movement of the other plunger.

4. Apparatus according to claim 3 wherein said fixture defines a base including a groove for receiving said first and third syringe barrels and means for securing said barrels in axial alignment and fixed axial position relative to each other.

5. Apparatus according to claim 1 wherein said first, second and third syringes are standard disposable medical syringes, each having approximately 50 cc capacity and said hose comprises ⅜ inch inside diameter flexible tubing.

6. Appratus according to claim 4 wherein each of said first and third syringe barrels has pairs of transverse wings at the end opposite the discharge end, and said fixture further comprises means for engaging said pairs of wings to fix the axial positions of said first and third barrels relative to each other.

7. Apparatus for injecting radiopaque dye during angiography comprising a hydraulic force transmission sub-system including a fluid conduit having opposite first and second ends and filled with hydraulic fluid, a drive piston at said first end of the conduit and a driven piston at said second end, whereby axial movement of the drive piston at a first rate causes corresponding movement of the driven piston, a syringe having a barrel for receiving a quantity of radiopaque dye, a plunger for driving the dye from the barrel, and needle means for introducing said dye from the barrel into a patient's artery, and a fixture for receiving and holding said syringe and for coupling said driven piston with said syringe plunger, whereby axial movement of said driven piston causes corresponding movement of said plunger.

* * * * *